United States Patent
Li et al.

(10) Patent No.: US 12,068,077 B2
(45) Date of Patent: Aug. 20, 2024

(54) APPLICATION OF ARTIFICIAL INTELLIGENCE ON DETECTING CANINE LEFT ATRIAL ENLARGEMENT ON THORACIC RADIOGRAPHS

(71) Applicant: THE REGENTS OF THE UNIVERSITY OF CALIFORNIA, Oakland, CA (US)

(72) Inventors: Shen Li, Davis, CA (US); Hao Cheng, Davis, CA (US); Erik R. Wisner, Davis, CA (US); Zigui Wang, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 413 days.

(21) Appl. No.: 17/596,848

(22) PCT Filed: Jun. 19, 2020

(86) PCT No.: PCT/US2020/038654
§ 371 (c)(1),
(2) Date: Dec. 20, 2021

(87) PCT Pub. No.: WO2020/257592
PCT Pub. Date: Dec. 24, 2020

(65) Prior Publication Data
US 2022/0351854 A1  Nov. 3, 2022

Related U.S. Application Data

(60) Provisional application No. 62/864,919, filed on Jun. 21, 2019.

(51) Int. Cl.
*G16H 50/20* (2018.01)
*G06T 7/00* (2017.01)
*G16H 30/00* (2018.01)

(52) U.S. Cl.
CPC .......... *G16H 50/20* (2018.01); *G06T 7/0012* (2013.01); *G16H 30/00* (2018.01);
(Continued)

(58) Field of Classification Search
CPC ......... A61B 2018/00541; G16H 30/20; G16H 30/40; G06T 7/0012; G06T 2207/10116; G06T 2207/10072; G06T 2207/30048
See application file for complete search history.

(56) References Cited

U.S. PATENT DOCUMENTS 5,251,626 A   10/1993  Nickolls et al.
5,622,171 A    4/1997  Asada et al.
(Continued)

FOREIGN PATENT DOCUMENTS

WO    2014198753 A1   12/2014
WO    2019153039 A1    8/2019

OTHER PUBLICATIONS

"Vetology AI: Your New Long-Term Teleradiology Solution", Web page <https://vetology.ai/#telerad>, 3 pages, 2010.
Chen et al.: "Thorax Disease Diagnosis Using Deep Convolutional Neural Network," 2016 38th Annual International Conference of the IEEE Engineering in Medicine and Biology Society (EMBC), Aug. 16-20, 2016, 6 pages.
Quinton et al.: "The reliability of chest radiographs in predicting left atrial enlargement," Cardiovascular Journal of Africa, vol. 21, No. 5, Oct. 31, 2010, 6 pages.
(Continued)

*Primary Examiner* — Gerald Johnson
(74) *Attorney, Agent, or Firm* — Stoel Rives LLP (57) ABSTRACT

A computer-executed method implementing a deep learning technique is carried out to perform on canine thoracic radiographic images an automated diagnosis of left atrial enlargement as an early sign of myxomatous mitral valve insufficiency.

12 Claims, 6 Drawing Sheets

(52) U.S. Cl.
CPC ............... *G06T 2207/10116* (2013.01); *G06T 2207/20084* (2013.01); *G06T 2207/30048* (2013.01)

(56) References Cited

U.S. PATENT DOCUMENTS

| | | | |
|---|---|---|---|
| 5,873,824 A | 2/1999 | Doi et al. | |
| 2017/0323481 A1 | 11/2017 | Tran et al. | |
| 2021/0287365 A1* | 9/2021 | Lu | G06V 10/764 |
| 2022/0084233 A1* | 3/2022 | Pak | A61B 6/481 |

OTHER PUBLICATIONS

Salguero et al.: "A radiographic measurement of left atrial size in dogs," Irish Veterinary Journal, 71, No. 25, Dec. 17, 2018, 7 pages.

Singh, et al.: "Bronchomalacia in Dogs with Myxomatous Mitral Valve Degeneration", Journal of Veterinary Internal Medicine, vol. 26, No. 2, Feb. 15, 2012, 9 pages.

Soto-Bustos et al.: "Diagnostic accuracy of electrocardiogramave related parameters in the assessment of left atrial size in dogs with degenerative mitral valve disease," The Journal of Veterinary Medical Science, vol. 79, No. 10, Aug. 28, 2017, 8 pages.

\* cited by examiner

APPLICATION OF ARTIFICIAL INTELLIGENCE ON DETECTING CANINE LEFT ATRIAL ENLARGEMENT ON THORACIC RADIOGRAPHS

COPYRIGHT NOTICE

© 2020 Regents of the University of California. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

This disclosure relates to methods of diagnosing left atrial enlargement that afflicts canine patients and, in particular, to a method implementing a deep learning technique to detect left atrial enlargement on canine thoracic radiographs.

BACKGROUND INFORMATION

Approximately ten percent of canine patients presented to veterinary general practitioners have heart disease. Myxomatous mitral valve disease (MMVD), the most common acquired progressive cardiac disorder, accounts for approximately 75% of these canine patients. Left atrial enlargement (LAE) is a relatively early sign for myxomatous mitral valve insufficiency. Canine patients with myxomatous mitral valve disease initially develop degenerative lesions of the mitral valve, which lead to left atrial enlargement and ultimately result in congestive heart failure (CHF). Early detection of left atrial enlargement and initiation of appropriate medical management delay the onset of congestive heart failure in dogs for an average of 15 months, which is more than 10% of average lifespan of most canine patients. Accurate diagnosis of MMVD and specific detection of LAE, an early feature of some canines with MMVD, therefore may be essential for appropriate initial medical management and to assess risk of heart failure and prognosis.

Currently, diagnostic evaluation of this disorder requires thoracic radiographs for preliminary screening and echocardiography, the latter typically performed by a veterinary cardiologist, for confirmation of a diagnosis. The most definitive screening test, the use of echocardiography for monitoring left atrial enlargement as a sentinel feature of myxomatous mitral valve disease, is expensive and limited in availability. To date, clinically applicable methods to identify left atrial enlargement from thoracic radiographs include detection of subjective cardiac margin changes, carinal elevation, subjective mainstream bronchial widening, tracheal bifurcation angle measurements, and vertebral heart score estimations. None of these diagnostic methods are, however, considered consistently accurate, particularly when they are carried out by general practice veterinarians. Moreover, radiographic reports prepared by veterinary radiologists and echocardiographic examinations performed by veterinary cardiologists are not immediately available to veterinary general practitioners. Thoracic radiographic examination is more easily performed and is widely available, but the interpretive skill of veterinary general practitioners varies.

The use of deep learning, an artificial intelligence technique, in automated diagnosis from radiographic images may match or exceed human expert performance in recognition of highly heterogeneous diagnostic images of human patients. The deep learning technique has been used in human medicine with success to detect end stage diabetic retinopathy and to accurately differentiate radiographs of human patients with tuberculosis from normal controls, given a sufficiently large training dataset. Deep learning has been used in computer-assisted medical imaging diagnosis in human medicine but not in veterinary medicine.

SUMMARY OF THE DISCLOSURE

The disclosed method implements a deep learning model to classify left atrial enlargement characteristics on thoracic radiographs of canine patients. The deep learning technique is applied to detect left atrial enlargement on thoracic radiographs to identify early mitral valve disease in canine patients and thereby document the potential of artificial intelligence as an affordable, fast, and reliable tool for assisted veterinary medical imaging diagnosis. The deep learning model is tuned to achieve equivalent or higher accuracy in detecting left atrial enlargement from canine thoracic radiographs as compared to that achieved by veterinary radiologists. The deep learning model provides an objective evaluation tool that is suitable for use by a veterinary general practitioner who need only perform a conventional thoracic radiographic examination to obtain the lateral thoracic view necessary to enable automated imaging diagnosis. The result of the automated imaging diagnosis is a definitive prediction of positive or negative indication of left arterial enlargement or material grounds for referral to a cardiologist for clinical evaluation.

Additional aspects and advantages will be apparent from the following detailed description of preferred embodiments, which proceeds with reference to the accompanying drawings.

DETAILED DESCRIPTION OF PREFERRED EMBODIMENTS

The disclosed method preferably uses the VGG deep learning open framework from the Visual Geometry Group, Department of Engineering Science, University of Oxford, supporting the Keras library, which is suitable for use in canine thoracic radiographic image analysis. The VGG framework and the deep learning package Keras are described in Simonyan, K., & Zisserman, A. (2015), *Very Deep Convolutional Networks for Large-Scale Image Recognition*, Conference Paper at ICLR 2015. The VGG framework uses fully convolutional networks for pixel prediction in performing inference of left atrial enlargement of canine patients. Keras is a high-level neural networks application program interface (API) written in Python 3 general purpose programming language. Although the VGG deep learning framework is used in describing a preferred embodiment of the disclosed method, other deep learning framework architectures could be used. A suitable deep learning framework architecture has building blocks for assembling deep convolutional layers, max-pooling layers, and encoder and decoder networks designed for large-scale image recognition.

The deep learning process for determining canine left atrial enlargement characteristics incorporates the general approach implemented in the VGG framework by using the Keras package from https://keras.io/. In system training, a lateral view thoracic radiographic image is acquired for each canine patient presented for training, followed by a contemporaneously performed (i.e., within about three days) echocardiographic examination by a veterinary cardiologist. The canine lateral view thoracic radiographic images show image patterns of left atrial enlargement sought to be identified and classified. The images showing left atrial size are labeled by a veterinary cardiologist, designating each of them with a left atrial enlargement positive or negative classification, based on standard echocardiographic criteria, including left atrial diameter and size and aortic root diameter and size, applied to a report on the contemporaneous echocardiographic examination. In an example, the dataset used in system training was taken from medical records of the University of California, Davis, Veterinary Medical Teaching Hospital from 2010-2017. These records were screened for canine patients that had a thoracic radiographic examination and a contemporaneous echocardiographic examination performed within 72 hours of the radiographic study. All radiographs were acquired using the same radiographic units with Digital Imaging and Communication in Medicine (DICOM®) output. From this dataset, patients were included in the investigation if the radiographic examination included a right lateral view and the radiographic and echocardiographic examinations included a formal report reviewed by a board-certified radiologist or cardiologist, respectively. Patients were excluded if the echocardiographic report was equivocal or ambiguous in determination of LAE or if an abridged echocardiographic examination was performed with no mention of left atrial size. For assessment of left atrial size, the standard institutional echocardiographic examination imaging protocol was used. The protocol includes a combination of subjective assessment and two linear left atrial measurements indexed to the aorta. One measurement involves the left atrium to aortic root ratio from a right parasternal short-axis view in early-diastole. The other left atrial size measurement involves maximum (end-systolic) left atrial dimension from a right a standard right parasternal long-axis four-chamber view, which is indexed to the aortic diameter measured in systole (annulus of the maximally opened aortic valve cusps) from a standard right parasternal long-axis left ventricular outflow tract view. Images were designated as being echocardiographically "positive" or "negative" for LAE based on conclusions in corresponding echocardiographic reports. Similarly, images were designated radiographically positive or negative, based on the corresponding radiology reports.

The method performed entailed downloading right lateral thoracic radiographic DICOM® images as Joint Photographic Experts Group (JPEG) file directly from the hospital Picture Archiving and Communication System (PACS) server with no initial alteration of native matrix size. Image file size can range from 63 KB to 439 KB, and image matrix size ranged from 1096 by 576 pixels to 2688 by 2208 pixels, depending on the size and detector density of the radiographic detector plate used during image acquisition. All annotations were removed from the native DICOM® images prior to transfer.

A machine learning specialist having access to the image files selects a model, learning rate (and other hyperparameters), and batch size, and thereafter trains the system. The VGG framework models are complete machine learning systems for inference and learning. The computation follows from the model definition for each of positive or negative classification of canine left atrial enlargement. Model definition entails presenting input data information relating to many hundreds of thoracic radiographic images of canine patients. The input data information for use by the VGG framework is that which is needed to run on a central processing unit (CPU), such as an Intel® 8 Core™ i7 processor, or a graphics processing unit (GPU), such as NVidia P40 GPU, for training. An application specific integrated circuit (ASIC) or field programmable gate array (FPGA) may be a suitable alternative to a GPU. The VGG framework trains the deep learning system by applying the labeled radiographic images to the convolutional neural network and assigning a set of weights for the pixels. A deep learning algorithm implemented by the VGG framework generalizes by establishing a set of weights that reclassify the radiographic image data presented. This inference and learning process entails thousands of iterations in the training process to minimize error. A machine learning specialist repeatedly evaluates the solution until an acceptable error rate is achieved.

Figure 1:
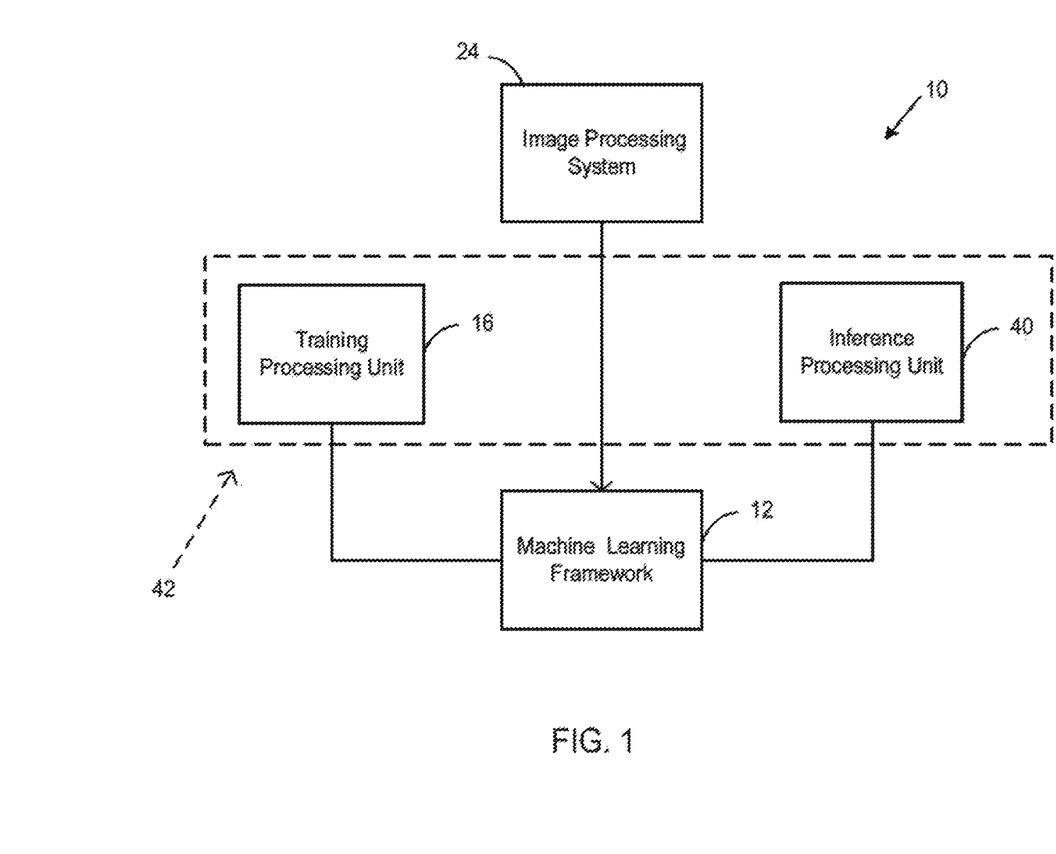
FIG. 1 is a block diagram showing the components of a system for practicing the disclosed method using deep learning techniques in automated diagnosis of canine left atrial enlargement from radiographic images.
Figure 2:
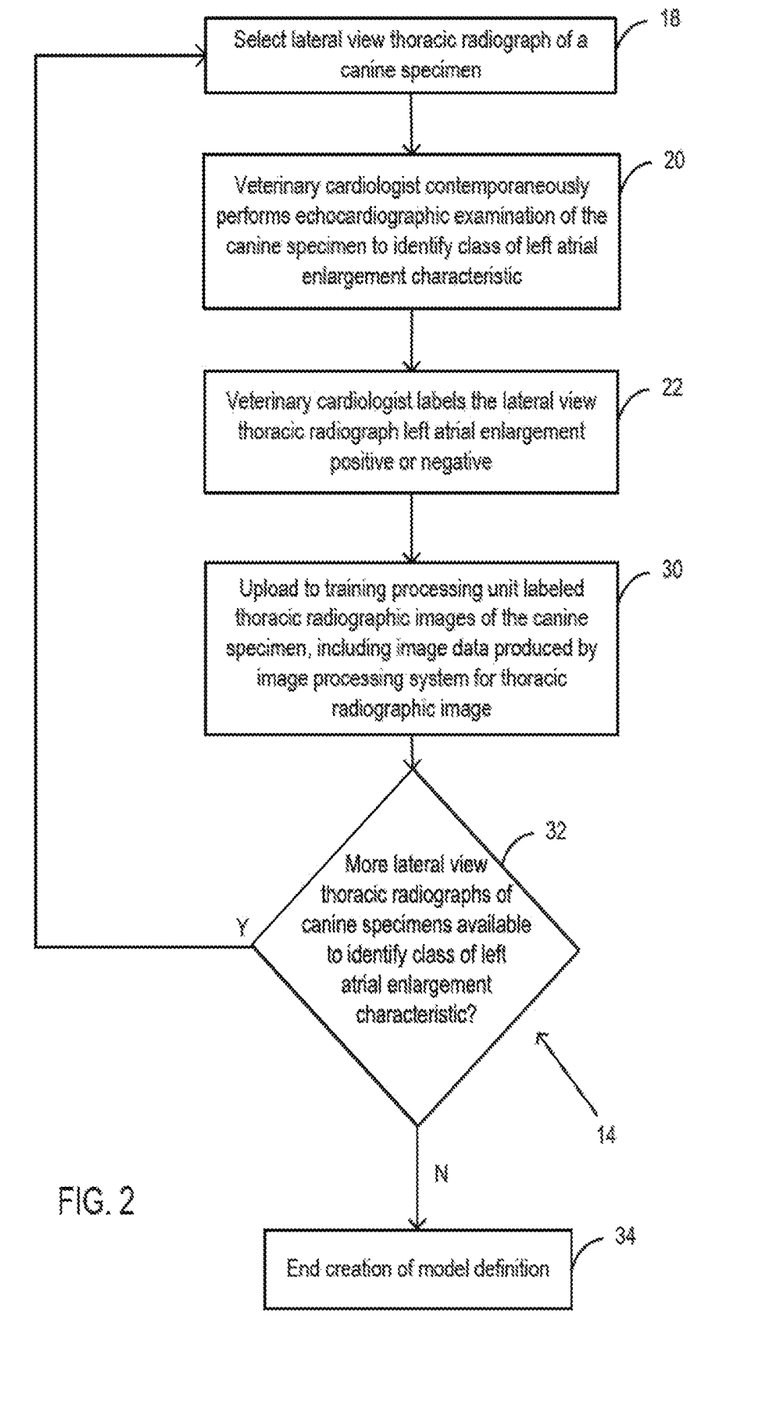
FIG. 2 is a flow diagram of the steps performed to train the machine learning system of FIG. 1 configured for canine left atrial enlargement recognition from labeled lateral view canine thoracic radiographic images.

FIG. 1 is a block diagram showing the components of a system 10 configured for practicing a preferred embodiment of the disclosed method of canine left atrial enlargement automated diagnosis performed on a machine learning framework 12. FIG. 2 is a flow diagram 14 showing the steps performed to train system 10.

With reference to FIGS. 1 and 2, the process of training system 10 starts with creating a definition of left atrial enlargement characteristics of canine patients. This is accomplished by applying to a training processing unit 16 multiple labeled thoracic radiographic images identifying canine patient specimens (hereafter, "canine specimens") that have or do not have left atrial enlargement. The labeled thoracic radiographic images are obtained for analysis as follows. A process block 18 represents selection of a right lateral view thoracic radiograph of a canine specimen. A process block 20 indicates that a veterinary cardiologist performs contemporaneously an echocardiographic examination of the canine specimen that is the subject of the selected thoracic radiograph to identify the class of left atrial enlargement characteristic. A process block 22 indicates that the veterinary cardiologist labels the lateral view thoracic radiograph left atrial enlargement positive or negative.

Machine learning framework 12, which is preferably the VGG deep learning framework, receives labeled lateral view canine thoracic radiographic image information from an image processing system 24. The labeling process performed by a veterinary cardiologist creates a definition specifying classes of left atrial enlargement characteristics. An extraction process carried out by a CPU on the labeled data creates input layer image pixel data that are format-ready as respects compatibility with machine learning framework 12 to perform the training process. The input layer pixel data represent classes of the left atrial enlargement characteristics at predictable locations of regions of the canine thoracic radiographic images. Image processing system 24 produces raw image data representing a labeled lateral view canine thoracic radiographic image that identifies a left atrial enlargement positive or negative characteristic.

Machine learning framework 12 supports training processing unit 16 on which a set of deep learning algorithms developed to train a convolutional neural network (CNN) operates to perform left atrial enlargement recognition on the format-ready input layer pixel data. A process block 30 represents uploading to training processing unit 16 the labeled lateral view radiographic image of the canine specimen, including raw image data produced by image processing system 24 for the radiographic image. The uploaded image data include image data representing the left atrial enlargement characteristics of the canine specimen. Performing left atrial enlargement recognition determines network learned weights for collections of pixels corresponding to image patterns in the regions of the canine thoracic radiographic images. Edge information is included in the network learned weights.

A decision block 32 represents an inquiry whether a lateral view thoracic radiograph of another canine specimen is available for analysis to determine classification of left atrial enlargement characteristics. If another thoracic radiograph of a canine specimen is available for analysis, the left atrial enlargement characteristic definition creation process resumes, as indicated by process block 18. Upon completion of the analysis of thoracic radiographs of all canine specimens to classify their left atrial enlargement characteristics, the machine learning training is complete and ends, as indicated by a process block 34.

With reference to FIG. 1, machine learning framework 12 supports an inference processing unit 40 that receives raw image data representing images of non-labeled canine thoracic radiographic images exhibiting left atrial enlargement characteristic features. Inference processing unit 40 delivers the raw image data to the trained convolutional neural network, which produces a series of probability maps corresponding to different ones of the classes of left atrial enlargement characteristics. The series of probability maps assists in developing a solution identifying which ones of the left atrium characteristic features belong to classes of left atrial enlargement characteristics and specifying the classes to which the identified left atrium characteristic features belong. Each of training processing unit 16 and inference processing unit 40 includes functionality of a CPU for formatting and similar data organization tasks and capability of a GPU for fast processing of large quantities of data, which the set of deep learning algorithms manipulates. The output provides a prediction of whether the canine patient has left atrial enlargement disorder.

Training processing unit 16 and inference processing unit 40 are encompassed by a dashed line box 42 to indicate that they may be separate processing units or combined in a single integrated processing unit. If training processing unit 16 and inference processing unit 40 are integrated as part of a single processing unit, it would have a capability to perform deep learning functions.

Set forth below is a specific example of system 10 implementing machine learning framework 12 on which the disclosed method is performed. Detecting the defining characteristics of left atrial enlargement in canine patients to facilitate diagnosis of this disorder from radiographic images by machine learning techniques entailed labeling many example right lateral thoracic view images. In this example, medical records of canine patients with both thoracic radiographs and contemporaneous echocardiograms performed were reviewed. Right lateral radiographic images were collected and used to train, validate, and test the disclosed convolutional neural network (CNN) algorithm. A total of 792 radiographic images having 281 echocardiographically positive and 511 echocardiographically negative for LAE were used in this example. The latest 81 images were used as a test set, and the remaining 711 images were used to train the algorithm. Accuracy, sensitivity, and specificity parameters were compared with those developed by board-certified veterinary radiologists. The accuracy achieved with the CNN algorithm used in this example to predict left atrial enlargement is 82.71%. The 82.71% accuracy is the same as that achieved by the board-certified veterinary radiologists.

The VGG framework was applied using the deep learning package Keras (version 2.3.0). The model structure was composed of 13 convolution layers, 5 pooling layers, 1 drop out layer, and 2 dense layers, with a total of 7,861,032 parameters. The following model parameters were used for training: 32 batch size, 100 epochs, and 0.0001 learning rate. The same padding technique was used in the model to improve the use of pixels on the edge of the image. The Adam optimization algorithm and 0.01 kernel regularizer were used.

Figure 3:
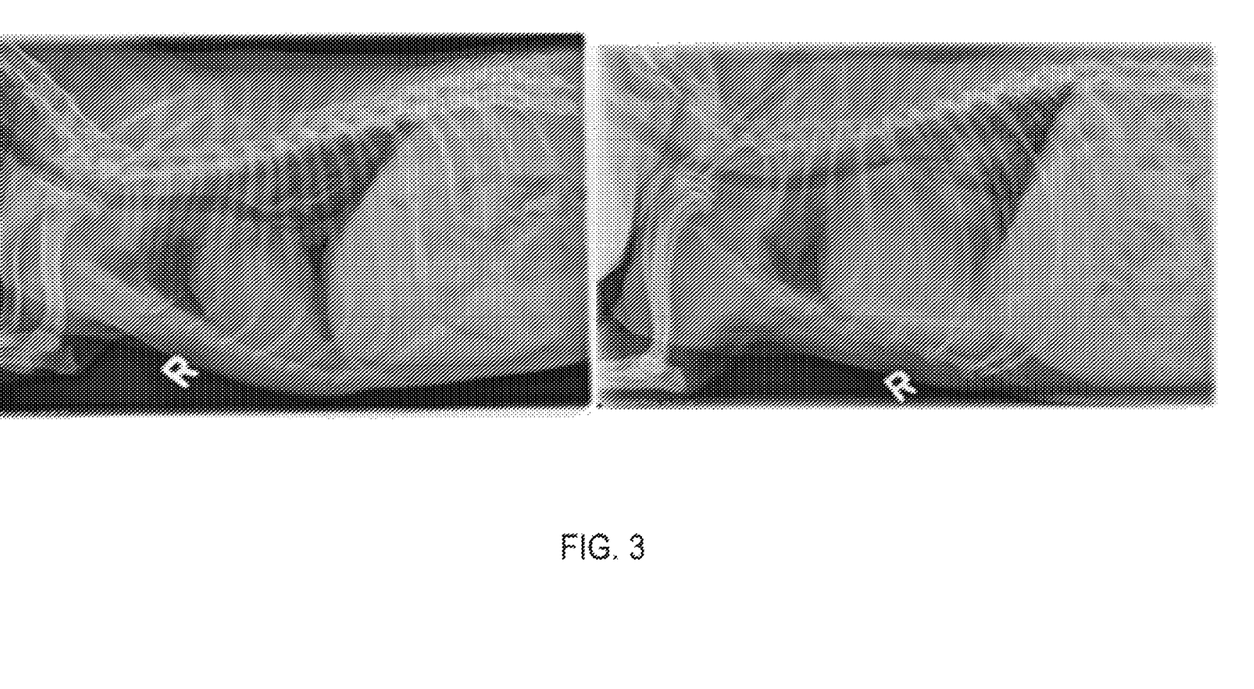
FIG. 3 shows two side-by-side right lateral view canine thoracic radiographs demonstrating negative (left side) and positive (right side) classifications of left atrial enlargement.

The radiographic images, with image size range from 63 KB to 439 KB and pixel range from 1096 by 576 pixels to 2688 by 2208 pixels, were resized to a matrix of 64×64 pixels. The pre-processing time, including loading and resizing, required less than one minute for each image. Of the total 792 images, the latest 81 images, according to the date the images were taken, were chosen for testing, among which 19 were positive and 62 were negative. FIG. 3 shows two representative radiographic images exemplifying negative and positive classifications. The remaining 711 images were randomly split into 10 groups of approximately equal size. These 711 images were then randomly split into training sets to train the deep learning algorithm to recognize left atrial enlargement pattern, validating sets to tune parameters in the algorithm. A cross-validation strategy was applied, in which each group is in turn used for validation and the remaining for training. The ten well-tuned deep learning models obtained from cross-validation were used to evaluate the prediction performance in the testing dataset, and the prediction results were averaged from these ten models. The image was predicted as the probability to be positive, and a probability above 0.5 was interpreted as "positive prediction." The testing dataset was used to assess the diagnostic accuracy, sensitivity, and specificity.

Two distinct loss functions were used to train the model including accuracy-driven function and sensitivity-driven function. Prediction accuracy and sensitivity were used as the training goal in these two functions. Results from the model were compared with those from veterinary radiologists.

Accuracy is calculated as $(A+D)/(A+B+C+D)$; sensitivity is calculated as $A/(A+B)$; and specificity is calculated as $D/(C+D)$. The calculations for these three parameters are set forth in Table 1.

TABLE 1

Contingency table

|  | Predict positive | Predict negative |
| --- | --- | --- |
| True Positive | A-true positive | B-false negative |
| True Negative | C-false positive | D-true negative |

In addition, the heart regions were cropped from all original images using the following criteria: visible cranial margin of the heart, visible caudal margin of the heart, ventral margin of the spine, and dorsal margin of the sternum. The analysis was performed using the same techniques and models. The results were very similar to the results obtained using the entire image size. The detailed results revealed that there was almost no difference between two approaches using uncropped and cropped data.

Figure 4:
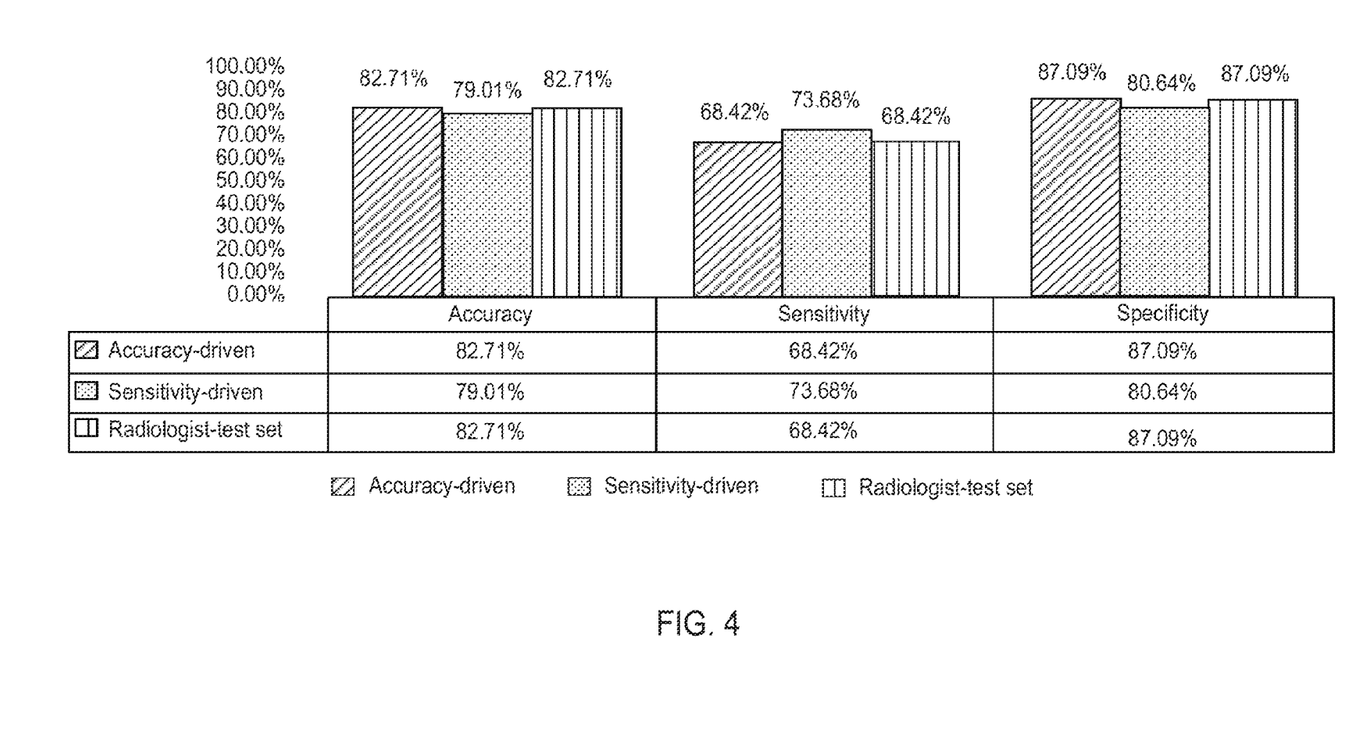
FIG. 4 is a set of bar graphs showing a comparison of overall accuracy, sensitivity, and specificity performance achieved by the disclosed method and veterinary radiologists in determining canine left atrial enlargement.

In the accuracy-driven CNN model, of the 81 images in the test set, 13 positive images were predicted positive, 8 positive images were predicted negative, 6 negative images were predicted positive, and 54 negative images were predicted negative (Table 2). The overall accuracy is 82.71%, sensitivity is 68.42%, and specificity is 87.09% (FIG. 4).

TABLE 2

Prediction result of accuracy-driven CNN model

|  | Predict positive | Predict negative | Total |
| --- | --- | --- | --- |
| True Positive | 13 | 6 | 19 |
| True Negative | 8 | 54 | 62 |
| Total | 21 | 60 | 81 |

In the sensitivity-driven CNN model, of the 81 images in the test set, 14 positive images were predicted positive, 5 positive images were predicted negative, 12 negative images were predicted positive, and 50 negative images were predicted negative (Table 3). The overall accuracy of sensitivity-driven CNN model is 79.01%, sensitivity is 73.68%, and specificity is 80.64% (FIG. 4).

TABLE 3

Prediction result of sensitivity-driven CNN model

|  | Predict positive | Predict negative | Total |
| --- | --- | --- | --- |
| True Positive | 14 | 5 | 19 |
| True Negative | 12 | 50 | 62 |
| Total | 26 | 55 | 81 |

For board-certified veterinary radiologists, of the 792 images in the entire data set, 208 positive images were predicted positive, 73 positive images were predicted negative, 64 negative images were predicted positive, and 447 negative images were predicted negative based on radiologists radiographic reports (Table 4).

TABLE 4

Performance of radiologists for the entire dataset (n = 792)

|  | Radiologist positive | Radiologist negative | Total |
| --- | --- | --- | --- |
| True Positive | 208 | 73 | 281 |
| True Negative | 64 | 447 | 511 |
| Total | 272 | 520 | 792 |

For board-certified veterinary radiologists, of the 81 images in the test set, the performance of radiologists was as follows: 13 positive images were predicted positive, 6 positive images were predicted negative, 8 negative images were predicted positive, and 54 negative images were predicted negative (Table 5). The accuracy is 82.71%, sensitivity is 68.42%, and specificity is 87.09% (FIG. 4).

The accuracy of the board-certified radiologist is the same as that of the accuracy-driven prediction CNN model. While a radiologist achieves higher sensitivity in the test set, the accuracy-driven CNN model holds higher specificity. The sensitivity-driven CNN model has higher sensitivity than that achieved by the radiologists in the test set.

TABLE 5

Performance of radiologists in the testing dataset (n = 81)

|  | Predict positive | Predict negative | Total |
| --- | --- | --- | --- |
| True Positive | 13 | 6 | 19 |
| True Negative | 8 | 54 | 62 |
| Total | 21 | 60 | 81 |

FIG. 4 shows the comparison of performance of accuracy-driven CNN model, sensitivity-driven CNN model, and board-certified radiologists. The accuracy, sensitivity, and specificity from the accuracy-driven CNN model were identical to those from radiologists; however, the individual data points were interpreted differently.

The prediction result from the accuracy-driven CNN model was compared with the performance of radiologists. There was agreement of the CNN model prediction and radiologist determination in 69 out of the 81 cases, resulting in 85% congruence. Among these 69 predictions, the CNN model and the radiologist were both incorrect in 8 instances and were both correct for the other 61 predictions. The false positive rate and false negative rate from CNN models and the radiologists were similar. Detailed prediction results are shown in Table 6.

TABLE 6

Congruency between accuracy-driven model and veterinary radiologists

|  | True positive | True negative | Agreement |
| --- | --- | --- | --- |
| Radiologist+/CNN+ | 12 | 3 | Concordant |
| Radiologist−/CNN− | 5 | 49 | Concordant |
| Radiologist+/CNN− | 1 | 5 | Discordant |
| Radiologist−/CNN+ | 1 | 5 | Discordant |

Figure 5:
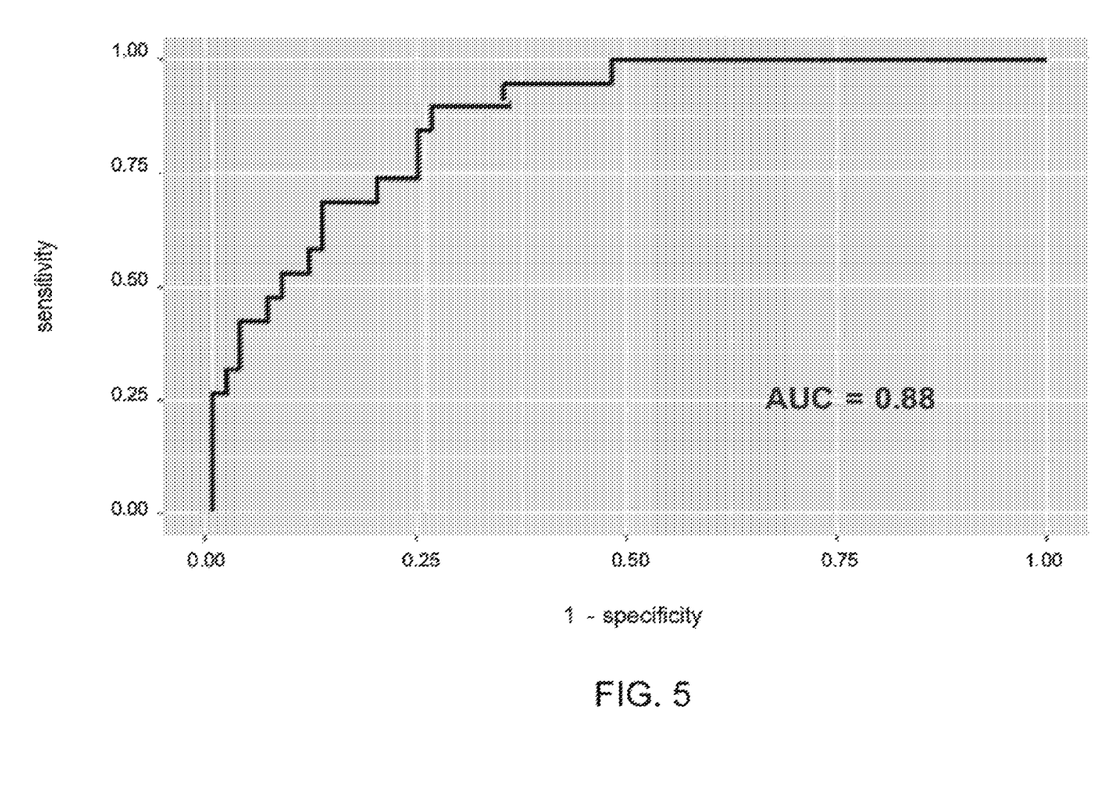
FIG. 5 shows a receiver operating characteristic curve and areas under the curve of "Accuracy-driven CNN model."
Figure 6:
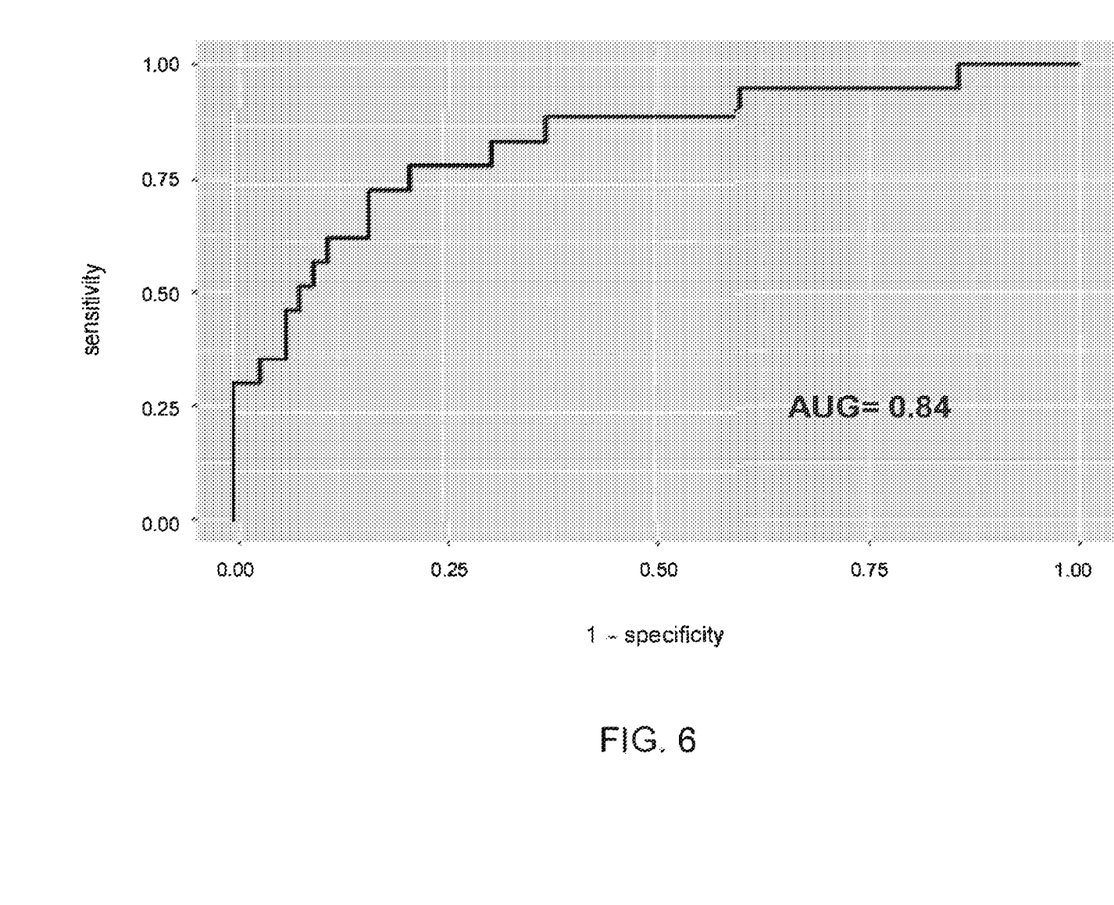
FIG. 6 shows a receiver operating characteristic curve and areas under the curve of "Sensitivity-driven CNN model."

The receiver operating characteristic curves and areas under the curve (AUC) for the accuracy-driven CNN model and the sensitivity-driven CNN model are shown in FIGS. 5 and 6. The AUC for the accuracy-driven CNN model is 0.88, and the AUC for the sensitivity-driven model is 0.84.

In this example, the CNN model was trained and validated with 64×64 pixels, pre-labeled single right lateral images. Besides these images, veterinary radiologists evaluated more information including patient's history and three-view images with higher resolutions (at least 1000×500 pixels). However, given such limited information, the CNN model was able to consistently achieve similar accuracy to, and sometimes higher sensitivity than, that achieved by the veterinary radiologists. As the amount of data used to train the model increases, including number of canine patients, the number of views of images, and image resolution, the disclosed CNN model may achieve higher accuracy, sensitivity, and specificity. The CNN model provides an objective evaluation tool that can consistently improve itself by feeding more echocardiograph-validated images.

The algorithm used for this study provides a percent likelihood of a positive result (presence of LAE) for a given image. For CNN data of this type, there are a number of practical applications including flagging a patient's imaging study as "high-risk" for follow-up review by a specialist, serving as a second "over-read" following a primary clinician or specialist interpretation or simply serving as a fully automated screening or diagnostic test.

A number of clinically applicable approaches have been used to assess LAE from thoracic radiographs including subjective evaluation of cardiac contours, tracheal bifurcation angle measurements, and vertebral left atrial size. It can be difficult to achieve consistent accuracy by using these methods, in large part, due to inherent limitations of the thoracic radiographic examination for assessment of LAE. Confounding variations in the appearance of the cardiac silhouette are caused by breed variability, patient positioning differences, cardiac and respiratory phase, and cardiac and noncardiac co-morbidities, among other parameters. Inconsistent assessment can also be the result of inter-reader or intra-reader interpretation variability. The use of echocardiographic findings as a standard for left atrial size can have its own inherent limitation as the CNN model relies on the examination and interpretation of echocardiographs. A potential problem of the CNN is the overfitting, particularly when the dataset is small. The dropout layer technique is applied to prevent it. The CNN model described herein provides an objective evaluation tool that can consistently improve itself by continually expanding the training dataset of echocardiograph-validated images.

It will be obvious to those having skill in the art that many changes may be made to the details of the above-described embodiments without departing from the underlying principles of the invention. The scope of the present invention should, therefore, be determined only by the following claims.

The invention claimed is:

1. A computer-executed method, implemented by machine learning techniques practiced on a machine learning framework, of performing on canine thoracic radiographic images an automated diagnosis of canine left atrial enlargement as an early sign of myxomatous mitral valve insufficiency, comprising:

providing, to the machine learning framework, evaluation input layer pixel data representing a thoracic radiographic image of a canine patient undergoing evaluation, the machine learning framework supporting a training processing unit in which is performed a set of deep learning algorithms developed to train a machine-learning based convolutional neural network on non-linear filter capturing of image structures for object recognition, the set of deep learning algorithms performing object recognition on data corresponding to labeled input layer pixel data to determine network learned weights to recognize canine left atrial enlargement characteristics learned from specimen thoracic radiographic images of multiple canine patient specimens, the specimen thoracic radiographic images represented by input layer pixel data and presented in a lateral thoracic view identifying the canine left atrial enlargement characteristics;

the labeled input layer pixel data representing each of the multiple canine specimen thoracic radiographic images to indicate whether left atrial enlargement of the canine patient is classified as left atrial enlargement positive or negative; and applying the evaluation input layer pixel data representing the thoracic radiographic image of the canine patient to the convolutional neural network operating on an inference processing unit, the convolutional neural network performing object recognition on the evaluation input layer pixel data to determine probability values relating to different classes of left atrial enlargement characteristics of the canine patient undergoing evaluation, and the inference processing unit deriving, from the probability values determined for the classes of left atrial enlargement characteristics, a prediction designating whether the canine patient undergoing evaluation exhibits a left atrial enlargement positive or negative classification.

2. The method of claim 1, in which the labeling of the input layer pixel data is based on standard electrocardiography parameters, including left atrial diameter and size and aortic root diameter and size, determined from contemporaneously acquired specimen thoracic echocardiographic images of the multiple canine patient specimens.

3. The method of claim 2, in which the left atrial size is assessed in accordance with a protocol that includes first and second linear left atrial size measurements indexed to the aorta, the first left atrial size measurement entailing determination of a left atrium-to-aortic root ratio from a right parasternal short-axis view in early diastole, and the second left atrial size measurement entailing an end-systolic left atrial dimension from a standard right parasternal long-axis four chamber view.

4. The method of claim 1, in which the lateral thoracic view identifying the canine left atrial enlargement characteristics is a right lateral view.

5. The method of claim 1, in which the input layer pixel data represent the classes of left atrial enlargement characteristics at predictable locations of regions of the canine thoracic radiographic images.

6. The method of claim 1, in which the inference processing unit includes functionality of a central processing unit (CPU) for data organizing tasks and capability of a graphics processing unit (GPU) for fast processing of large quantities of data the set of deep learning algorithms manipulates.

7. A computer-executed method, implemented by machine learning techniques, of performing on canine thoracic radiographic images an automated diagnosis of canine left atrial enlargement as an early sign of myxomatous mitral valve insufficiency, comprising:

creating a definition of canine left atrial enlargement characteristics learned from thoracic radiographic images of multiple canine patients, the thoracic radiographic images represented by input layer pixel data and presented in a lateral thoracic view identifying the canine left atrial enlargement characteristics;

labeling the input layer pixel data representing each of the multiple canine thoracic radiographic images to indicate whether left atrial enlargement of the canine patient is classified as left atrial enlargement positive or negative;

receiving, by a machine learning framework, the labeled input layer pixel data representing the multiple canine thoracic radiographic images, the machine learning framework supporting a training processing unit in which is performed a set of deep learning algorithms developed to train a machine-learning based convolutional neural network on non-linear filter capturing of image structures for object recognition, the set of deep learning algorithms performing non-linear filter capturing image structures for object recognition on data corresponding to the labeled input layer pixel data to determine network learned weights to recognize canine left atrial enlargement characteristics;

providing, to the machine learning framework, evaluation input layer pixel data representing a thoracic radiographic image of a canine patient undergoing evaluation; and applying the evaluation input layer pixel data to the convolutional neural network operating on an inference processing unit, the convolutional neural network performing object recognition on the evaluation input layer pixel data to determine probability values relating to different classes of left atrial enlargement characteristics of the canine patient undergoing evaluation, and the inference processing unit deriving, from the probability values determined for the classes of left atrial enlargement characteristics, a prediction designating whether the canine patient undergoing evaluation exhibits a left atrial enlargement positive or negative classification.

8. The method of claim 7, in which the labeling of the input layer pixel data is based on standard electrocardiography parameters, including left atrial diameter and size and aortic root diameter and size, determined from contemporaneously acquired specimen thoracic echocardiographic images of the multiple canine patients.

9. The method of claim 8, in which the left atrial size is assessed in accordance with a protocol that includes first and second linear left atrial size measurements indexed to the aorta, the first left atrial size measurement entailing determination of a left atrium-to-aortic root ratio from a right parasternal short-axis view in early diastole, and the second left atrial size measurement entailing an end-systolic left atrial dimension from a standard right parasternal long-axis four chamber view.

10. The method of claim 7, in which the lateral thoracic view identifying the canine left atrial enlargement characteristics is a right lateral view.

11. The method of claim 7, in which the input layer pixel data represent the classes of left atrial enlargement characteristics at predictable locations of regions of the canine thoracic radiographic images.

12. The method of claim 7, in which the inference processing unit includes functionality of a central processing unit (CPU) for data organizing tasks and capability of a graphics processing unit (GPU) for fast processing of large quantities of data the set of deep learning algorithms manipulates.

* * * * *